United States Patent [19]
Discko, Jr.

[11] Patent Number: 5,954,996
[45] Date of Patent: Sep. 21, 1999

[54] DENTAL ETCH AND PACKAGE THEREFOR

[75] Inventor: John J. Discko, Jr., Hamden, Conn.

[73] Assignee: Centrix, Inc., Shelton, Conn.

[21] Appl. No.: 08/680,136

[22] Filed: Jul. 15, 1996

Related U.S. Application Data

[63] Continuation-in-part of application No. 08/275,003, Jul. 13, 1994, Pat. No. 5,660,273.

[51] Int. Cl.$^6$ .......................... C09K 13/00; C09K 13/04; C09K 13/06
[52] U.S. Cl. .................... 252/79.1; 252/79.2; 252/79.4
[58] Field of Search ................... 252/79.1, 79.2, 252/79.4

[56] References Cited

U.S. PATENT DOCUMENTS

| | | | |
|---|---|---|---|
| 3,618,751 | 11/1971 | Rich | 206/47 R |
| 3,759,375 | 9/1973 | Nappi | 206/361 |
| 3,835,834 | 9/1974 | Brown et al. | 206/229 |
| 4,066,566 | 1/1978 | Lauster | 252/136 |
| 4,786,534 | 11/1988 | Aiken | 206/229 |
| 4,838,851 | 6/1989 | Shabo | 604/1 |
| 4,880,311 | 11/1989 | Bagwell et al. | 206/209.1 |
| 4,889,228 | 12/1989 | Gueret | 206/229 |
| 5,001,803 | 3/1991 | Discko, Jr. | 15/167.1 |
| 5,106,297 | 4/1992 | Discko, Jr. | 433/77 |
| 5,112,152 | 5/1992 | McBride | 206/229 |
| 5,184,719 | 2/1993 | Gordon | 206/209.1 |
| 5,240,415 | 8/1993 | Haynie | 433/216 |

FOREIGN PATENT DOCUMENTS

| | | |
|---|---|---|
| 35714 | 7/1985 | Hungary . |
| 60-075409 | 4/1985 | Japan . |

*Primary Examiner*—R. Bruce Breneman
*Assistant Examiner*—George Goudreau
*Attorney, Agent, or Firm*—Fattibene and Fattibene; Arthur T. Fattibene; Paul A. Fattibene

[57] ABSTRACT

This disclosure relates to an anhydrous dental etchant composition that includes a mixture of phosphoric acid or an equivalent and anhydrous glycerin having a final acid concentration in the range of 10% to 40%, and having a trace of a color indicator therein; and a unit package and dispenser for the anhydrous dental etch that includes an applicator and a predetermined amount of anhydrous etchant which is self contained for single patient application and which can be readily disposed of after use.

13 Claims, 1 Drawing Sheet

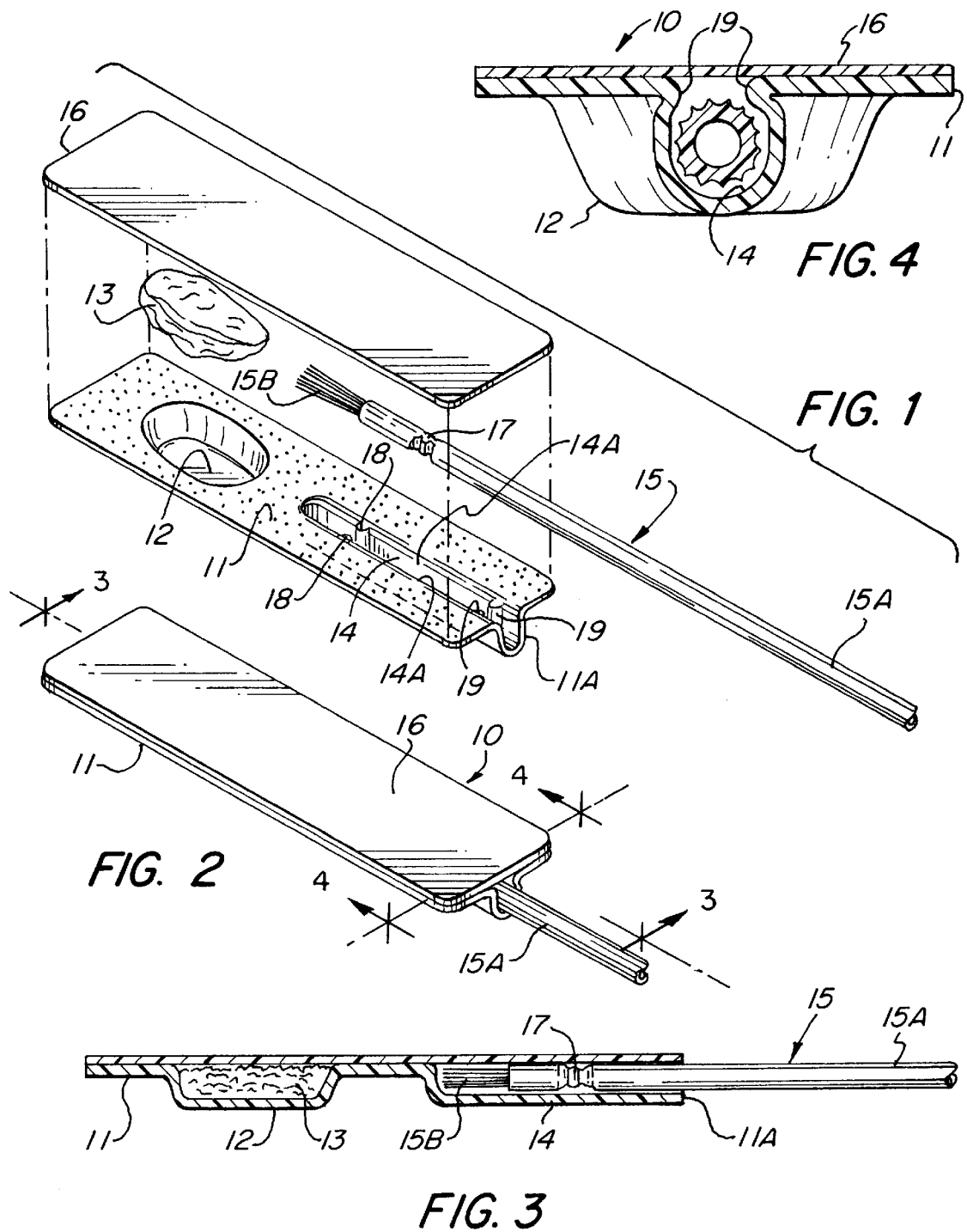

DENTAL ETCH AND PACKAGE THEREFOR

RELATED APPLICATION

This application includes common subject matter relating to and constitutes a continuation-in-part application of a application Ser. No. 08/275,003 filed Jul. 13, 1994, now U.S. Pat. Ser. No. 5,660,273.

FIELD OF THE INVENTION

This invention relates generally to a dental etch, and more specifically to an anhydrous dental etch and a package therefor.

PROBLEM AND PRIOR ART

Etchants were first introduced into dentistry in the late 1960's. Initially, such dental etches comprised simply a clear phosphoric acid diluted with water to lessen the concentration. Etchants containing phosphoric acid have been found to be most satisfactory for etching or roughing the enamel surfaces of a tooth. Resin bonding for effecting a tooth restoration is best effected by first etching the enamel surface of the tooth. This is because the etching roughens the surface area of the tooth to provide for a micro-mechanical interlocking of the resin-bonding material to the etched surface of the tooth. Phosphoric acid cut or diluted by water was very fluid and tended to run. Such fluid etches had the disadvantage of uncontrollable flow over the surface of the tooth and frequently migrate or run onto the gum or surrounding mouth tissues, which could cause potential injury to the patient if extreme care was not used.

Initially, it was believed that phosphoric acid etch was not suitable for use on dentin. This was because it was believed that a phosphoric acid etchant on dentin would cause tooth sensitivity and possible pulpal injury. To obviate this fear, phosphoric acid etchants were thickened with silica and packaged in a syringe to facilitate the precise placement of the etch so as to keep the etch away from dentin. U.S. Pat. No. 4,802,950 discloses a phosphoric acid etch thickened with silica to form a phosphoric acid gel.

In the late 1980's, the all-etch technique became popular. Based on clinical studies, it was shown that one could etch dentin and seal it with bonding material with no noticeable hypersensitivity or pulpal death. As a result, dental etch need not be made very viscous or formed as a thick gel or require syringe placement.

In the past, it has also been noted that water with which phosphoric acid etch was cut or diluted tended to evaporate or dry out in time. This was the source of a considerable problem in that such etch would tend to thicken over time, and that any loss of water by evaporation would increase the concentration of the acid that could result in injury to a patient if allowed to come into contact with the sensitive mouth tissues. Also, it was very troublesome for the dentist to accurately apply such thickened or viscous acid gel because of difficulty with its flow characteristics.

SUMMARY OF THE INVENTION

This invention contemplates a dental etch that includes a mixture of phosphoric acid or an equivalent and glycerin to result in an etch composition having a final acid concentration range of 10% to 40%. This is attained by mixing a solution of phosphoric acid or equivalent having a greater than 40% concentration with a water soluble anhydrous material, e.g. glycerin, according to the formula:

$$Y = \frac{X \times V \times 100}{A}$$

where Y equals solution of phosphoric acid or equivalent; A equals acid concentration greater than 40% of initial acid solution; X equals desired percent or concentration of phosphoric acid or equivalent; and V equals volume desired and the amount of anhydrous glycerin equals V−Y. A trace of a suitable dye substance such as methylene blue or equivalent may be added to the composition to function as a color indicator. Because glycerin is anhydrous, the resultant etchant composition does not include any excess water which can evaporate to change the resultant viscosity and/or the acid concentration of the final etch composition over time. As the etch composition is water soluble, it can easily be rinsed or washed away to enhance its rinse ability. Other acids such as citric acid, maleic acid, orthophosphoric acid, acetic acid and the like may be substituted for phosphoric acid, and it is so understood herein when reference is made to phosphoric acid. This invention also contemplates a unique single dose package to facilitate the marketing, use and application of the improved etch composition. The package comprises a molded container formed from a plastic sheet having an indented well for receiving and storing therein a predetermined amount of the described etchant sufficient for a single patient or application. The container is also formed with another indented portion to define a seat for containing a suitable applicator or brush by which a dentist may apply the etchant onto a tooth surface as desired. A releasable cover sheet is adhesively secured to the container so formed to seal and maintain the etchant within the indented well and the associated applicator or brush within its indented seat until readied for use. The formula may also be dispensed from a conventional push syringe or squeeze bottle.

IN THE DRAWINGS

FIG. 1 illustrates a perspective view of an acid etchant package embodying the invention.

FIG. 2 is a perspective exploded view of the acid etchant package of FIG. 1.

FIG. 3 is a sectional view taken along FIG. 3—3 on FIG. 1.

FIG. 4 is a sectional view taken along line 4—4 on FIG. 4.

DETAILED DESCRIPTION

To obviate the foregoing noted problems, this invention is directed to a dental etch composition comprising of a phosphoric acid or the like mixed with a predetermined amount of an anhydrous glycerin or other compatible water soluble anhydrous material to result in a final etch composition having an acid concentration in the range of 10% to 40%. A trace of a suitable dye, such as methylene blue, may also be incorporated into the mixed acid and glycerin formulation, described herein, to function as a color indicator. It will be understood that other water soluble dyes may be used in lieu of methylene blue as a color indicator. The purpose of the color indicator is to assist a dentist in determining when the treated tooth has been washed clean of all acid etch after an etching process is completed. The composition or etch embodying the invention can be readily made simply by a mechanical mixing of the desired percentages of the primary ingredients, such as the phosphoric acid or its equivalent and glycerin, as herein specified.

According to this invention, the acid etch composition for use on teeth comprises e.g. a phosphoric acid mixed with anhydrous glycerin so as to attain a final phosphoric acid concentration in the range of 10% to 40%. Using an 87% phosphoric acid solution, as for example, the acid etch embodying this invention is formulated in accordance with the following formula:

$$Y = \frac{X \times V \times 100}{A}$$

or $$Y = \frac{X \times V \times 100}{87}$$

wherein

Y=amount of starting acid solution

A=initial solution acid concentration in percentage

X=desired percentage of acid concentration in final composition

V=the desired volume of etch composition and the anhydrous glycerin equals V−Y.

Utilizing the above formula, a liter of acid etch composition containing a 40% concentration of phosphoric acid embodying the present invention comprises:

| | |
|---|---|
| 87% phosphoric acid solution based on acidimetry | 0.460 liters |
| Anhydrous glycerin | 0.540 liters |

A liter of acid etch composition embodying the present invention containing a 10% concentration of phosphoric acid comprises:

| | |
|---|---|
| 87% phosphoric acid solution | 0.115 liters |
| Anhydrous glycerin | 0.885 liters |

The foregoing etch compositions can be readily formed at room temperature simply by the appropriate mixing of the respective ingredients in a suitable mixer.

To facilitate the use of the foregoing described acid etch composition, a color indicator may be added to the mixture. The color indicator may comprise a suitable water soluble dye. A methylene blue has been found to be a suitable color indicator. Methylene blue in the amount of approximately 0.167 grams per liter of etchant, mixed as described herein, has been found to be sufficient to provide the etchant with the desired color indicating ability. The function of the color indicator is to render the areas where the etchant has been applied readily visible to the dentist. Also, the color indicator functions to indicate when all of the acid etch has been washed away or rinsed from the etched tooth.

In use, the tooth or teeth to be etched are thoroughly cleaned. Thereafter, with the aid of a suitable applicator or brush, the dentist applies the described etchant to the tooth. The described etchant, being more fluid and having better wetting characteristics than the known acid gel type etchants, can readily flow and etch the tiny nooks and crannies not reachable by the conventional gel type etchants. Depending upon the phosphoric acid concentration of the described etchant, etching of the tooth will occur within 15 to 60 seconds, and the rinsing or washing can be achieved within 15 to 20 seconds.

In accordance with the present invention, the described etch composition is preferably packaged in a unit dose package 10 that is formed of a readily moldable plastic sheet of material 11 having an indented well 12 formed therein to form a container for containing a predetermined volume of etchant 13, formulated as described herein, sufficient for a single application. The plastic sheet 11 is also formed with an elongated indented portion to define a seat 14 to contain an applicator in the form of a small brush 15 by which the dentist can simply brush the etchant 13 contained in the well 12 onto a tooth where desired. A readily releasable sealing cover 16, adhesively secured to the plane of the plastic sheet 11, secures the etchant 13 and associated applicator 15 within their respective indented well 12 and seat 14 to complete the single dose etchant package 10. After treatment, the dentist simply discards the entire package, including the applicator.

In the illustrated embodiment, the seat 14 is defined as a relatively narrow indentation having opposed side walls 14A–14B and which indentation terminates at one edge or periphery 11A of the plastic sheet. The illustrated applicator or brush 15 may comprise a brush of the type disclosed in U.S. Pat. No. 5,001,803, which includes an elongated tubular handle 15A having a tuft of bristles 15B inserted at one end of the handle 15A and which handle 15A is provided with a flexible hinge 17 formed adjacent the brush end 15B so that a dentist can readily angle the brush end 15B relative to the elongated handle 15A to facilitate the placement of the etchant. In the illustrated embodiment, the flexible hinge 17 defines a reduced portion adjacent the brush end 15B.

To retain the applicator handle 15A within its seat 14, the seat is provided with opposed inwardly extending protrusions 18 which, when the brush is disposed within its seat 14, will extend into the reduced portion of the handle. Thus, the protrusions 18—18 will function to prevent the applicator brush 15 from being inadvertently linearly separated or pulled from the package.

The seat 14 may also be formed at the upper end of the sidewalls 14A, 14B with inwardly extending end portions 19—19 that extend toward one another to define a space slightly less than the diameter of the brush handle 15A so that the handle is snap fitted within the seat 14. The arrangement is such that end portions 19—19 resist any unintentional lateral separation of the applicator or brush 15 from its seat 14, until used.

Securing the supply of acid etchant 13 and the applicator 15 within their respective well 12 and seat 14 is a releasable cover sheet 16 which is adhesively secured to the marginal or planar portions of the sheet 11. The arrangement is such that when a dentist effects the removal of the cover sheet 16 to uncover the acid etch 13, the applicator or brush 15 can be readily released from its seat 14.

Assuming the tooth to be etched has been suitably cleaned, the dentist removes the applicator 15 from its seat 14 and applies the acid etchant 13 to the tooth as needed. Upon completion of the etching procedure, the dentist disposes of the package 10 and applicator 15. Thus, any cross-contamination is completely obviated as the described package is designed for use for only one patient.

While the present invention has been described with respect to a particular embodiment, modifications and variations may be made without departing from the spirit or scope of this invention.

What is claimed is:

1. An improved dental etchant comprising a mixture of tooth etching acid and glycerin having an acid concentration ranging between 10% to 40%, wherein said glycerin comprises greater than 50% of the dental etchant.

2. An improved dental etchant as defined in claim 1 and including a color indicator.

3. An improved dental etchant as defined in claim 2 wherein said color indicator comprises methylene blue.

4. An improved dental etchant comprising the formula of:

$$Y = \frac{X \times V \times 100}{A}$$

wherein
- Y=amount of acid solution having concentration greater than 40%
- A=starting solution acid concentration
- X=desired acid concentration in final etch composition
- V=volume desired and an anhydrous material equal to Y−V.

5. The improved dental etchant as defined in claim 4 and including a color indicator.

6. The improved dental etchant as defined in claim 5 wherein said color indicator equals 0.167 grams per liter.

7. The improved dental etchant as defined in claim 6 wherein said color indicator comprises methylene blue.

8. A dental etchant comprising:
   0.460 liters of 87% phosphoric acid solution, and
   0.540 liters of anhydrous glycerin.

9. A dental etchant as defined in claim 8 and including a color indicator.

10. A dental etchant as defined in claim 9 wherein said color indicator includes approximately 0.167 grams of methylene blue per liter.

11. A dental etching composition comprising:
   a phosphoric acid solution having a concentration ranging from ten to forty percent; and
   a quantity of glycerin comprising more than fifty percent of the dental etching composition.

12. A dental etching composition as in claim 11 wherein:
   the dental etching composition is contained in a unit dose package.

13. A dental etching composition as in claim 12 further comprising:
   an applicator retained within said unit dose package.

* * * * *